United States Patent
Detjen et al.

(10) Patent No.: US 10,661,258 B2
(45) Date of Patent: May 26, 2020

(54) IN-SITU TRIM COKE SELECTIVATION OF TOLUENE DISPROPORTIONATION CATALYST

(71) Applicant: ExxonMobil Chemical Patents Inc., Baytown, TX (US)

(72) Inventors: Todd E. Detjen, Houston, TX (US); Xiaobo Zheng, Houston, TX (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 244 days.

(21) Appl. No.: 14/888,725

(22) PCT Filed: Apr. 30, 2014

(86) PCT No.: PCT/US2014/036071
§ 371 (c)(1),
(2) Date: Nov. 3, 2015

(87) PCT Pub. No.: WO2014/200626
PCT Pub. Date: Dec. 18, 2014

(65) Prior Publication Data
US 2016/0074845 A1 Mar. 17, 2016

Related U.S. Application Data

(60) Provisional application No. 61/834,549, filed on Jun. 13, 2013.

(51) Int. Cl.
| | |
|---|---|
| *B01J 29/06* | (2006.01) |
| *C07C 6/12* | (2006.01) |
| *B01J 29/03* | (2006.01) |
| *B01J 29/04* | (2006.01) |
| *B01J 35/02* | (2006.01) |
| *B01J 35/00* | (2006.01) |
| *B01J 37/02* | (2006.01) |
| *B01J 37/00* | (2006.01) |
| *B01J 29/40* | (2006.01) |
| *B01J 37/08* | (2006.01) |
| *C07C 2/86* | (2006.01) |
| *C07C 5/27* | (2006.01) |

(52) U.S. Cl.
CPC ............ *B01J 29/06* (2013.01); *B01J 29/03* (2013.01); *B01J 29/04* (2013.01); *B01J 29/041* (2013.01); *B01J 29/40* (2013.01); *B01J 35/0006* (2013.01); *B01J 35/023* (2013.01); *B01J 37/0009* (2013.01); *B01J 37/0217* (2013.01); *B01J 37/0219* (2013.01); *B01J 37/08* (2013.01); *C07C 2/864* (2013.01); *C07C 2/865* (2013.01); *C07C 5/2729* (2013.01); *C07C 6/123* (2013.01); *B01J 2229/12* (2013.01); *B01J 2229/123* (2013.01); *B01J 2229/32* (2013.01); *B01J 2229/36* (2013.01); *C07C 2529/06* (2013.01); *C07C 2529/08* (2013.01); *C07C 2529/18* (2013.01); *C07C 2529/40* (2013.01); *C07C 2529/65* (2013.01); *C07C 2529/70* (2013.01); *Y02P 20/52* (2015.11)

(58) Field of Classification Search
CPC . B01J 29/03; B01J 29/04; B01J 29/041; B01J 29/06; B01J 29/40; B01J 2229/12; B01J 2229/123; B01J 2229/32; B01J 2229/36; B01J 35/023; B01J 35/0006; B01J 37/08; B01J 37/0215; B01J 37/0217; B01J 37/0219; B01J 37/0009
USPC ........................... 502/60, 63, 64, 69, 77, 85
See application file for complete search history.

(56) References Cited

U.S. PATENT DOCUMENTS

| | | |
|---|---|---|
| 3,698,157 A | 10/1972 | Allen et al. |
| 4,060,568 A | 11/1977 | Rodewald |
| 4,090,981 A | 5/1978 | Rodewald |
| 4,100,215 A | 7/1978 | Chen |
| 4,127,616 A | 11/1978 | Rodewald |
| 4,145,315 A | 3/1979 | Rodewald |
| 4,283,306 A | 8/1981 | Herkes |
| 4,379,761 A | 4/1983 | Olson et al. |
| 4,443,554 A | 4/1984 | Dessau |
| 4,465,886 A | 8/1984 | Rodewald |
| 4,477,583 A | 10/1984 | Rodewald |
| 4,487,843 A | 12/1984 | Telford et al. |
| 4,522,929 A | 6/1985 | Chester et al. |
| 4,548,914 A | 10/1985 | Chu |
| 4,559,314 A | 12/1985 | Shihabi |
| 4,927,979 A | 5/1990 | Yamagishi et al. |
| 4,950,835 A | 8/1990 | Wang et al. |
| 5,173,461 A | 12/1992 | Absil et al. |
| 5,367,099 A * | 11/1994 | Beck ....................... B01J 29/40 502/85 |

(Continued)

FOREIGN PATENT DOCUMENTS

EP  296582  12/1988

OTHER PUBLICATIONS

Bauer et al., "Improvement of coke-induced selectivation of H-ZSM-5 during xylene isomerization", Microporous and Mesoporous Materials, 47, 2001, pp. 67-77.*

(Continued)

*Primary Examiner* — Elizabeth D Wood

(57) ABSTRACT

The invention relates to treating a molecular sieve prepared by at least one in situ selectivation sequence wherein graphitic coke is adhered to said molecular sieve, which is useful in a toluene disproportionation process.

19 Claims, No Drawings

(56) References Cited

U.S. PATENT DOCUMENTS

| | | | | |
|---|---|---|---|---|
| 5,382,737 A | * | 1/1995 | Beck | B01J 29/40 585/470 |
| 5,403,800 A | * | 4/1995 | Beck | B01J 29/40 502/62 |
| 5,476,823 A | * | 12/1995 | Beck | B01J 29/40 502/60 |
| 5,516,956 A | * | 5/1996 | Abichandani | B01J 29/44 585/475 |
| 5,574,199 A | * | 11/1996 | Beck | B01J 29/40 585/400 |
| 5,675,047 A | * | 10/1997 | Beck | B01J 29/40 502/63 |
| 5,689,027 A | * | 11/1997 | Abichandani | B01J 29/40 585/481 |
| 5,705,726 A | * | 1/1998 | Abichandani | B01J 29/40 585/481 |
| 5,726,114 A | | 3/1998 | Chang et al. | |
| 5,773,679 A | * | 6/1998 | Beck | C07C 6/123 585/470 |
| 6,013,849 A | | 1/2000 | Drake et al. | |
| 6,133,470 A | * | 10/2000 | Beck | C07C 6/123 560/77 |
| 6,207,871 B1 | * | 3/2001 | Hellring | C07C 5/2767 585/475 |
| 6,486,373 B1 | * | 11/2002 | Abichandani | B01J 29/04 502/60 |
| 6,576,582 B1 | * | 6/2003 | Beck | B01J 29/40 502/63 |
| 6,777,583 B2 | * | 8/2004 | Beck | B01J 29/40 208/46 |
| 9,162,942 B2 | | 10/2015 | Beech, Jr. et al. | |
| 2001/0051754 A1 | * | 12/2001 | Lissy | B01J 29/40 585/319 |
| 2010/0048382 A1 | | 2/2010 | Xie et al. | |
| 2012/0071317 A1 | | 3/2012 | Butler et al. | |

OTHER PUBLICATIONS

Chen et al., "Para-Directed Aromatic Reactions over Shape-Selective Molecular Sieve Zeolite Catalysts", Journal of the American Chemical Society, vol. 101, pp. 6783-6784.

Pines, "The Chemistry of Catalytic Hydrocarbon Conversions", Academic Press, NY, p. 72, 1981.

\* cited by examiner

IN-SITU TRIM COKE SELECTIVATION OF TOLUENE DISPROPORTIONATION CATALYST

CROSS REFERENCE TO RELATED APPLICATIONS

This application is a National Stage Application of International Application No. PCT/US2014/036071, filed Apr. 30, 2014, which claims the benefit of priority from U.S. Provisional 61/834,549, filed Jun. 13, 2013, which is incorporated herein by reference.

FIELD OF THE INVENTION

The invention relates to modification of a catalyst for toluene disproportionation.

BACKGROUND OF THE INVENTION

The term "shape-selective catalysis" describes unexpected catalytic selectivities in zeolites. The principles behind shape selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective alkyl-substituted benzene disproportionation to para-dialkyl-substituted benzene.

A representative para-dialkyl-substituted benzene is para-xylene. The production of para-xylene is typically performed by methylation of toluene or by toluene disproportionation over a catalyst under conversion conditions. Examples include the reaction of toluene with methanol, as described by Chen et al., J. Amer. Chem. Soc. 101, 6783 (1979), and toluene disproportionation, as described by Pines in "The Chemistry of Catalytic Hydrocarbon Conversions" Academic Press, N.Y., 1981, p. 72. Such methods typically result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent". For example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568, 5,476,823 and 3,698,157 disclose specific methods for contacting a catalyst with a selectivating agent containing silicon ("silicon compound").

Various organic compounds have been employed as carriers for silicon to compounds in the silicon impregnation methods applied to zeolite catalysts. For example, U.S. Pat. Nos. 4,145,315, 4,127,616, 4,090,981 and 4,060,568 describe the use of inter alia $C_{5-7}$ alkanes as solvents for silicon impregnation.

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ pre-selectivation of zeolites has involved single applications of the modifying compound. It may be noted, however, that the suggestion of multiple treatments was made in U.S. Pat. No. 4,283,306 to Herkes. The Herkes patent discloses the promotion of crystalline silica catalyst by application of an amorphous silica such as tetraethylorthosilicate. The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that multiple ex situ selectivation confers no benefit and in fact reduces a catalyst's efficacy in shape-selective reactions.

Steaming has also been used in the preparation of zeolite catalysts to modify the alpha or improve stability. For example, U.S. Pat. No. 4,559,314 describes steaming a zeolite/binder composite at 200-500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

However, a need still exists for novel catalysts to achieve disproportionation of aromatic compounds to provide, for example, para-xylene in good yields and/or selectivity.

SUMMARY OF THE INVENTION

Modified silicon selectivated molecular sieves and methods for modification are described. Shape selective hydrocarbon conversion processes over a modified catalyst are also described.

In one embodiment, a silicon selectivated catalyst is modified in situ by at least one in situ trim coke selectivation sequence to provide a modified silicon selectivated molecular sieve, wherein graphitic coke is adhered to said molecular sieve by said in situ trim coke selectivation sequence.

In another embodiment, a molecular sieve is exposed to one or more ex situ selectivation sequences. Each selectivation sequence includes impregnating the catalytic molecular sieve with a silicon selectivating agent, followed by calcination after each impregnation. Selectivating agents useful herein include a large variety of silicon-containing compounds, preferably silicon polymers that in embodiments can be solubilized in organic carriers. In embodiments such organic carriers include various alkanes, and preferably include paraffins having 7 or more carbons.

The modification method further includes treating the calcined molecular sieve with an in situ trim selectivation to provide a graphitic coke adhered to the surface, pores or both of the sieve. The graphitic coke is considered "hard" in that it not easily rubbed off or removed from the modified molecular sieve. The in situ trim selectivating may be performed by coke trim selectivating wherein an organic compound is decomposed in the presence of the modified catalytic molecular sieve, at conditions suitable for decomposing the organic compound. An advantage is provided in embodiments whereby the in-situ coke selectivation takes only up to 7 days, whereas conventional long term selectivation can take greater than 6 months.

The modification method can further include hydrogen stripping of the graphitic containing silicon selectivated modified molecular sieve. Hydrogen stripping in general is used to remove coke from the modified molecular sieve. Our lab work shows that hydrogen stripping under the provided conditions, after the selectivation with silicon compounds and the in situ coke selectivation, removes a portion of the coke in such a manner that it positively impacts catalyst activity and the catalyst selectivity when operating at normal process conditions.

Catalytic molecular sieves modified by the methods described herein are provided. Processes for shape selective production of dialkyl-substituted benzenes by contacting a reaction stream comprising an alkylbenzene, under conversion conditions with a modified catalytic molecular sieve modified by the methods herein are also provided.

Advantageously, the modified catalyst has enhanced shape selectivity for para-dialkyl-substituted benzene production. Accordingly, the disproportionation process described herein exhibits increased selectivity for p-dialkylbenzene and may exhibit an increased alkyl-benzene disproportionation rate constant.

DETAILED DESCRIPTION

The present embodiments relate to modified molecular sieves useful in shape selective dialkyl-substituted benzene production reactions, and the method of their preparation.

The molecular sieves used herein can be a zeolite, e.g., an intermediate pore-size zeolite having a constraint index within the approximate range of 1 to 12 (e.g., zeolites having less than about 7 angstroms pore size, such as from about 5 to less than 7 angstroms) having a silica to alumina mole ratio of at least about 5, e.g., at least about 12, e.g., at least 20.

The silica to alumina mole ratio referred to may be determined by conventional analysis. This ratio is meant to represent, as closely as possible, the molar ratio in the rigid anionic framework of the zeolite crystal and to exclude silicon and aluminum in the binder (if present) or in cationic or other form within the channels.

Examples of intermediate pore size zeolites useful herein include ZSM-5 (U.S. Pat. No. 3,702,886 and U.S. Pat. No. Re. 29,948); ZSM-11 (U.S. Pat. No. 3,709,979), ZSM-5/ZSM-11 intermediate (U.S. Pat. No. 3,832,449); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-50 (U.S. Pat. No. 4,640,829; ZSM-57 (U.S. Pat. No. 5,046,685); and/or ZSM-58 (U.S. Pat. No. 5,417,780).

Other zeolites suitable for use in some embodiments described herein include zeolite beta, MCM-22 (U.S. Pat. No. 5,304,968), MCM-36 (U.S. Pat. No. 5,292,698), MCM-49 (U.S. Pat. No. 5,236,575), MCM-56 (U.S. Pat. No. 5,362,697), mordenite, MCM-58 (U.S. Pat. No. 5,437,855), synthetic and natural faujasites, and amorphous or ordered mesoporous materials such as MCM-41 (U.S. Pat. No. 5,098,684).

Additional molecular sieves which find utility in conjunction with the present embodiments include aluminophosphates, e.g., ALPO-5, VPI-5; silicoaluminophosphates, e.g., SAPO-5, SAPO-11, SAPO-30, SAPO-31, SAPO-34; and other metal aluminophosphates. These are variously described in U.S. Pat. Nos. 4,440,871; 4,554,143; 4,567,029; 4,666,875; and 4,742,033.

Further additional molecular sieves which find utility in embodiments described herein include ITQ-2, ITQ-3 (described in U.S. Pat. No. 6,500,404), ITQ-12 (described in U.S. Pat. No. 6,471,939), and ITQ-13 (described in U.S. Pat. No. 6,471,941). The structural types and references to the synthesis of these zeolites can be found in the "Atlas of Zeolite Framework Types" (published on behalf of the Structure Commission of the International Zeolite Association), by Ch. Caerlocher, W. M. Meier, and D. H. Olson, published by Elsevier, Fifth revised edition, 2002, which is hereby incorporated by reference. Structural types and references to the zeolites mentioned above are available on the World Wide Web at www.iza-structure.org. Such zeolites are commercially available from Zeolyst International, Inc.

In one aspect, a zeolite, either incorporated with a binder or in unbound form, is contacted one or more times with a selectivating agent, preferably between about two and about six times. The selectivating agent comprises a compound or polymer containing a main group or transition metal, preferably silicon. In each phase of the selectivation treatment, the selectivating agent is deposited on the external surface of the catalyst by any suitable method. For example, the selectivating agent, such as a silicon compound, may be dissolved in a carrier, mixed with the catalyst, and then dried by evaporation or vacuum distillation. This method is termed "impregnation". The molecular sieve may be contacted with the silicon compound at a molecular sieve/silicon compound weight ratio of from about 100/1 to about 1/100.

The catalysts described herein can be selectivated by a vapor phase process or a liquid phase process. An example of a liquid phase selectivation process is described herein as an ex situ selectivation process. Examples of ex situ selectivation techniques suitable for use in herein are provided in U.S. Pat. Nos. 5,367,099; 5,404,800; and 5,365,004. The ex situ selectivation treatment may result in the deposition of at least 1 wt. % of siliceous material on the zeolite. The treatment deposits siliceous material on the catalyst by contacting the catalyst with a silicon-containing selectivating agent. Subsequent to treatment with the selectivating agent, the catalyst may be conventionally calcined at temperatures, below, say, 600° C. or less, under conditions sufficient to remove organic material therefrom while leaving the siliceous material on the zeolite, preferably without reducing the crystallinity of the zeolite.

The catalyst may be ex situ selectivated by single or multiple treatments with a liquid organosilicon compound in a liquid carrier. Each treatment can be followed by to calcination of the treated material in an oxygen-containing atmosphere, e.g., air.

In accordance with embodiments, the multiple impregnation ex situ selectivation method, the zeolite is treated at least once, e.g., from 1 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. Suitable stable aqueous emulsions of organosilicon compounds (e.g., silicone oil) are described in U.S. Pat. No. 5,726,114 to Chang et al. These emulsions are generated by mixing the organosilicon oil and an aqueous component in the presence of a surfactant or surfactant mixture. Useful surfactants include any of a large variety of surfactants, including ionic and non-ionic surfactants. Preferred surfactants include non-nitrogenous, non-ionic surfactants such as alcohol, alkylphenol, and polyalkoxyalkanol derivatives, glycerol esters, polyoxyethylene esters, anhydrosorbitol esters, ethoxylated anhydrosorbitol esters, natural fats, oils, waxes and ethoxylated esters thereof, glycol esters, polyalkylene oxide block co-polymer surfactants, poly(oxyethylene-co-oxypropylene) non-ionic surfactants, and mixtures thereof. More preferred surfactants include octoxynols such as Octoxynol-9. Such preferred surfactants include the TRITON® X series, such as TRITON® X-100 and TRITON® X-305, available from Rohm & Haas Co., Philadelphia, Pa., and the Igepal® Calif series from GAF Corp., New York, N.Y. Emulsions formulated using such surfactants are effective for selectivating zeolites such as ZSM-5 to enhance shape selectivity, and to passivate surface acidity detrimental to product selectivity in certain regioselective catalytic applications such as the disproportionation of alkylbenzenes. Organosilicon compounds useful herein are water soluble and may be described as organopolysiloxanes. The preferred compounds are polyalkylene oxide modified organopolysiloxanes. The organopolysiloxanes are preferably larger than the pores of the catalyst and do not enter the pores.

Examples of methods of depositing silicon on the surface of the zeolite are found in U.S. Pat. Nos. 4,090,981, 4,127,616, 4,465,886 and 4,477,583 to Rodewald, which are incorporated by reference herein. Further examples of the deposition of a silicon compound on zeolite surfaces are described in H. Nakajima, M. Koya, H. Ishida, and M. Kohno, Sekiyu Gakkaishi, 35(2) (1992), and in U.S. Pat. No. 4,950,835 to Wang et al.

As was described above, the catalysts herein are ex situ selectivated by one or more multiple coatings with a high efficiency para-selectivating agent, each coating followed by calcination and optionally trim-selectivated with additional high efficiency para-selectivating agent. As used herein, the term "high efficiency para-selectivating agent" is used to indicate substances which will increase the para-selectivity of a catalytic molecular sieve to the stated levels in alkylbenzene disproportionation while maintaining commercially acceptable levels of alkylbenzene to dialkylbenzene conversion. Such substances include, for example, organic silicon compounds such as phenylmethyl silicone, dimethyl silicone, and blends thereof which have been found to be suitable.

The organosilicon compound selectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Suitable silicon-containing selectivating agent is selected from the group consisting of polysiloxanes, siloxanes, silanes, disilanes and alkoxysilanes. Representative ex situ selectivation silicone compounds include dimethyl silicone, diethyl silicone, phenylmethyl silicone, methylhydrogen silicone, ethylhydrogen silicone, phenylhydrogen silicone, methylethyl silicone, phenylethylsilicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenyl silicone, methylvinyl silicone, and ethylvinyl silicone. The ex situ selectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as liquid ex situ selectivating agents, as may silicones with other functional groups.

Preferred silicon-containing selectivating agents, particularly when the ex situ selectivating agent is dissolved in an organic carrier or emulsified in an aqueous carrier, include dimethylphenylmethylpolysiloxane (e.g., Dow-550®) and phenylmethyl polysiloxane (e.g., Dow-710®). Dow-550® and Dow-710® are available from Dow Chemical Company, Midland, Mich.

Water soluble organosilicon compounds are commercially available as, for example, SAG-5300®, manufactured by Union Carbide, Danbury Conn., conventionally used as an anti-foam, and SF 1188® manufactured by General Electric, Pittsfield, Mass.

When the organosilicon ex situ selectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as $N(CH_3)_3$, $N(C_2H_5)_3$, and $N(C_3H_7)_3$. A preferred water soluble organosilicon preselectivating agent is an n-propylamine silane, available as Hydrosil 2627® from Creanova (formerly Huls America), Somerset, N.J.

The organosilicon compound can be preferably dissolved in an aqueous solution in an organosilicon compound/$H_2O$ weight ratio of from about 1/100 to about 1/1.

A "solution" is intended to mean a uniformly dispersed mixture of one or more substances at the molecular or ionic level. The skilled artisan will recognize that solutions, both ideal and colloidal, differ from emulsions.

The catalyst can be contacted with a substantially aqueous solution of the organosilicon compound at a catalyst/organosilicon compound weight ratio of from about 100 to about 1, at a temperature of about 10° C. to about 150° C., at a pressure of about 0 psig to about 200 psig (0 Pa-g-1.38 MPa-g), for a time of about 0.1 hour to about 24 hours, the water is preferably removed, e.g., by distillation, or evaporation with or without vacuum, and the catalyst is calcined.

Additional suitable ex situ selectivating agents are disclosed in U.S. Pat. No. 5,849,968 to Beck et al.

Selectivation is carried out on the catalyst, e.g., by conventional ex situ treatments of the catalyst before loading into a hydrocarbon conversion reactor. Multiple ex situ treatments, 1 to 6 treatments, preferably 1 to 4 treatments, have been found especially useful to selectivate the catalyst. When the zeolite is ex situ selectivated by a single or multiple impregnation technique, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof, resulting from the residue of the organo portion of the organosilicon compound used to impregnate the catalyst.

Useful selectivating agents include siloxanes which can be characterized by the general formula:

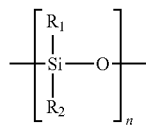

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxy silanes, such as tetramethoxy silane, may also be utilized. These useful silicon-containing selectivating agents include silanes characterizable by the general formula:

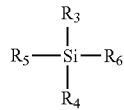

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

Preferably, the kinetic diameter of the high efficiency, p-xylene selectivating to agent is larger than the zeolite pore diameter, in order to avoid entry of the selectivating agent into the pore and any concomitant reduction in the internal activity of the catalyst.

Examples of suitable carriers for the selectivating silicon compound include linear, branched, and cyclic alkanes having five or more carbons. In one aspect, the carrier comprises a linear, branched, or cyclic alkane having a boiling point greater than about 70° C., and most preferably containing 7 or more carbons. Optionally, mixtures of low volatility organic compounds, such as hydrocracker recycle oil, may be employed as carriers. The most preferred low volatility hydrocarbon carriers of silicon selectivating agents are decane and dodecane.

It has been found that a multiple selectivation scheme provides unexpectedly increased efficiency of deposition of the silicon compound on the surface of the catalyst.

This increased efficiency allows for the use of relatively small quantities of the silicon compound as well as relatively small quantities of the carrier.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the carrying medium, the degree to which the zeolite has been dried prior to contact with the silicon compound, and to calcination of the zeolite.

After the selectivation sequence, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours.

The selectivated molecular sieve catalyst, with or without binder, can show improved selectivity upon steaming. Alternatively, excessive steaming can be detrimental to a selectivated catalyst.

An advantage of the present embodiments includes the formation of the graphitic hard coke in the second selectivation sequence. It was unexpected to find that the formation of hard coke on the surface and/or throughout the molecular sieve improved performance of the ex situ selectivated molecular sieve with silicon-containing selectivation agents. The hard coke produced from the trim selectivation process remains adhered to the surface and/or throughout the molecular sieve. In one aspect, when exposed to the given hydrogen stripping conditions, the coke remains on the catalyst in such a manner to positively impact selectivity with minimal to no activity loss compared to pre-second selectivation performance.

Typically a soft coke would be formed. "Soft" coke is coke that is removed at the hydrogen stripping conditions provided herein. The "hard" coke is either not removed or only partially removed under the hydrogen stripping conditions. The desired type of coke is left on the sieve by trim selectivating and then hydrogen stripping and the given set of conditions.

The term "trim selectivation" is well-known in the art per se and, while having been described slightly differently from time-to-time (see, for instance, U.S. Pat. Nos. 6,207,871; 5,495,059, and 5,321,183) as used herein the term means that a feed comprising a desired compound is passed over the molecular sieve under in situ selectivation conditions, said conditions sufficient to deposit a residue of the desired compound(s) on the molecular sieve. Thus, "trim coke selectivation" means that the molecular sieve has coke deposited thereon.

In yet another embodiment, the ex situ selectivated molecular sieve (treated with a silicon containing selectivating agent(s)), calcined, and subsequently trim selectivated can be subjected to hydrogen stripping. Hydrogen stripping is utilized to remove coke that is built up on a catalyst. However, in the present embodiments, hydrogen stripping does not significantly remove the graphitic coke and the coke remains in and/or on the molecular to sieve. Surprisingly, in one embodiment, it has been found to improve the activity of the catalysts and selectivity of the catalysts described herein.

Following in situ trim coke selectivation, hydrogen stripping at about from about 200° F. to about 1100° F. (93-593° C.), preferably below 1000° F. (about 538° C.), more preferably from about 850° F. to about 950° F. (454-510° C.), for at least 0.1 hour to about 72 hours, preferably from about 12 hours to about 48 hours, at a pressure of about 150 to about 500 psig (1.03 to 3.44 MPa-g), preferably from about 250 to about 350 psig (1.72 to 2.41 MPa-g), with a hydrogen purity greater than 1 mol %, preferably greater than 50 mol % is effective to remove the majority of coke while maintaining a portion of the coke is substantially graphitic and that was formed in such a manner that the catalyst activity is returned to near pre-trim selectivation values and catalyst selectivity is improved to higher than pre-trim selectivation values. It was surprising that the combination of in situ trim coke selectivation at given conditions followed by hydrogen stripping at the given conditions yielded improved sieve selectivity with minimal impact to sieve activity when compared to the pre-trim coke selectivation sieve performance. The graphitic coke is coke that is either not removed or only partially removed under the hot hydrogen conditions described above.

The hydrogen stripping step improves shape selectivity without significant activity loss.

There are also investment advantages for being able to perform the trim selectivation and hydrogen stripping at temperatures <1000° F. (<538° C.). At typical reactor operating pressures, temperatures >950-1000° F. (510-538° C.) typically require investment in a higher cost alloy for the reactor wall and other process equipment.

For example, the silicone selectivated catalyst, such as a 4-times silicone selectivated, silica-bound ZSM-5 "A" silica bound catalyst having no metals impregnated therein and is subjected to in situ trim coke selectivation. This in situ trim coke selectivation process involves a reactor temperature within the range of 500° F. to 1100° F. (260-593° C.), preferably below 1000° F. (538° C.), preferably 850-950° F. (454-510° C.), such as 900° F. (482° C.), (preferably involving increasing reactor temperature from toluene disproportionation operating conditions), for about 0.1 hour, preferably about 0.1 hour to about 3 weeks, operating at a weight hourly space velocity (WHSV) of about 0.1-20 hr$^{-1}$, preferably 1-3 hr$^{-1}$, such as 2 hr$^{-1}$ (e.g., 2 kg/hr feed: 1 kg catalyst) and a hydrogen partial pressure preferably in the range of from about 10-300 psia (0.0689-2.07 Mpa), more preferably 40-120 psia (0.276-0.827 Mpa) with a reactor pressure of about 250-350 psig (1.72-2.41 Mpa-g).

In embodiments, the modified silicon selectivated molecular sieve is then subjected to hydrogen stripping of the catalyst (with no hydrocarbon feed), preferably for about 12-48 hours, at a temperature range of from about 850° F. to about 950° F. (454-510° C.) at a pressure of from about 250 to about 350 psig (1.72-2.41 MPa-g). Note that WHSV units are "hr$^{-1}$" (reciprocal hours) and may be omitted herein for convenience; note also regarding pressure values that the suffix "g", such as "Pa-g" means "gauge pressure", whereas the suffix "a" or the absence of a suffix, means "actual pressure".

The catalyst described herein displays an increased para-xylene ratio to meta and ortho-xylene (90.7% para-xylene selectivity initially, 93.1% para-xylene selectivity after 1 week at trim selectivation conditions, 93.7% selectivity after 2 weeks at trim selectivation conditions). In addition, the ratio of benzene to xylene yield post trim selectivation and hydrogen stripping was unchanged from the initial yields. Furthermore, there was no significant change in reactor temperature and toluene conversion following trim selectivation when compared to initial reactor temperature and toluene conversion (765° F. (407° C.) reactor average temperature and 29.9% toluene conversion after two weeks of trim selectivation conditions and 24 hour hydrogen strip versus 769° F. (409° C.) reactor average temperature and 29.9% toluene conversion initially).

The high efficiency para-dialkylbenzene selectivating agent for trim-selectivation may comprise a silicon compound discussed in greater detail above. For example, organic silicon compounds such as phenylmethyl silicone, dimethyl silicone, and mixtures thereof are suitable. According to one embodiment, a silicone containing phenylmethylsilicone and dimethylsilicone groups in a ratio of about 1:1 is co-fed to the system, while the other components, e.g., alkylbenzene and hydrogen, are fed in the amounts set forth above. The high-efficiency para-dialkylbenzene selectivating agent is fed in an amount of from about 0.001 wt. % to about 10 wt. % of the alkylbenzene according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica to on the catalyst. During the selectivation procedure the para-selectivity of the catalyst will be observed to increase further. The silicon containing polymer or molecular species may be dissolved in toluene or other appropriate aromatic or hydrocarbon carrier.

Alternatively, the catalyst, prior to contacting with alkylbenzene under disproportionation conditions, may be subjected to trim-selectivation with a thermally decomposable organic compound at an elevated temperature in excess of the decomposition to temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, most preferably the alkylbenzene being subjected to disproportionation itself. In the latter case, the alkylbenzene is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the alkyl-benzene feed is continued in contact with the coke-containing catalyst under conditions of temperature and hydrogen concentration conducive to disproportionation, with a greatly reduced coking rate.

While not wishing to be bound by theory, it is believed that the advantages described herein are in part obtained by rendering acid sites on the external surfaces of the catalyst substantially inaccessible to reactants, while increasing catalyst tortuosity. Acid sites existing on the external surface of the catalyst are believed to isomerize the solution-phase p-dialkylbenzene back to an equilibrium level with the other two dialkylbenzene isomers, in the case of xylenes thereby reducing the amount of p-xylene in the xylenes to only about 24%. By reducing the availability of these acid sites to the solution-phase p-dialkylbenzene, the relatively high proportion of the para isomer can be maintained. It is believed that the high-efficiency, p-dialkylbenzene selectivating agents described herein block or otherwise render these external acid sites unavailable to the p-dialkylbenzene by chemically modifying said sites.

The near regioselective conversion of alkylbenzene to para-dialkylbenzene by disproportionating alkylbenzene in a reaction stream containing an alkylbenzene feed with a selectivated and optionally steamed catalytic molecular sieve, optionally in the presence of hydrogen, and at reaction conditions suitable to provide p-dialkylbenzene selectivity of greater than about 80%, preferably greater than 90% are included. The production stream may also contain small amounts of o- and m-dialkylbenzene and trace amounts of impurities.

As used herein, the term "para-dialkylbenzene selectivity" means the proportion of p-dialkylbenzene, indicated as a percentage, among all of the dialkylbenzene products, i.e., p-dialkylbenzene, o-dialkylbenzene, and m-dialkylbenzene. Those skilled in the art will appreciate that the relative proximity of the boiling points of these isomers necessitates relatively expensive separation processes for the isolation of p-dialkylbenzene. On the other hand, p-dialkylbenzenes are more readily separated from other components in the product stream such as benzene, monoalkylbenzenes and other alkyl-substituted benzenes.

As explained in greater detail herein, a process for obtaining p-dialkylbenzenes at alkylbenzene conversions of at least 10%, preferably at least about 15-35% with a p-dialkylbenzene selectivity of greater than 24%, preferably at least 90% is provided.

The alkylbenzene feedstock preferably includes about 50% to 100% alkylbenzene, more preferably at least about 80% alkylbenzene. Other compounds such as benzene and other alkyl-substituted benzenes may also be present in the toluene feedstock without adversely affecting the processes or catalysts described herein.

The alkylbenzene feedstock may also be dried, if desired, in a manner which will minimize moisture entering the reaction zone. Numerous methods known in the art are suitable for drying the alkylbenzene charge utilized herein. These methods include percolation through any suitable desiccant, for example, silica gel, activated alumina, molecular sieves or other suitable substances, the use of a cold box, the use of fractionation, or the use of liquid charge dryers.

The catalytic molecular sieves useful in accordance with the methods provided herein are preferably in the hydrogen form, prior to modification, but may be in the ammonium or sodium form. Preferably, the catalytic molecular sieve comprises an intermediate pore-size zeolite such as a ZSM-5, ZSM-11, ZSM-22, ZSM-23, or ZSM-35 as discussed above. The catalytic molecular sieves also preferably have a Constraint Index of about 1-12. The details of the method by which Constraint Index is determined are described fully in U.S. Pat. No. 4,016,218, incorporated herein by reference.

The crystal size of zeolites used herein is preferably greater than 0.1 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr (8 MPa) hydrocarbon pressure. The crystal size is computed by applying the diffusion equation given by J. Crank, "The Mathematics of Diffusion", Oxford at the Clarendon Press, 1957, pp. 52-56, for the rate of sorbate uptake by a solid whose diffusion properties can be 15 approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{1/2}.$$

In the present case these measurements have been made on a computer controlled, thermogravimetric electrobalance, but there are numerous ways one skilled in the art could obtain the data. The larger crystal material used herein has a sorption time, $t_{0.3}$, of 497 minutes, which gives a calculated crystal size of 1.6 microns. The smaller crystal material has a sorption time of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in The Journal of Catalysis, Vol. 4, pp. 522-529 (August 1965); Vol. 6, p. 278 (1966); and Vol. 61, p. 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," Nature, Vol. 309, No. 5959, pp. 589-591, 14 Jun. 1984). The experimental conditions of the test used herein include a constant temperature of 538° C. and a variable flow rate as described in detail in the Journal of Catalysis, Vol. 61, p. 395 (1980). The catalysts described herein preferably have an alpha value greater than 1, for example, from about 1 to about 2000. The alpha value of the catalyst may be increased by initially treating the catalyst with nitric acid or by mild steaming before pre-selectivation. This type of steaming is discussed in U.S. Pat. No. 4,326,994.

The silica to alumina ratio of the catalysts herein may be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 10,000 are useful, it is preferred to use zeolites having ratios of at least about 20 to about 2000.

For the improved disproportionation processes herein, the suitable molecular sieve may be employed in combination with a support or binder material such as, for example, a porous inorganic oxide support or a clay binder. While the preferred binders are alumina, silica or self-bound, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 30% to about 98% by weight and is preferably from about 50% to about 80% by weight of the composition. The composition may be in the form of an extrudate, beads or fluidizable microspheres.

Operating conditions employed in the processes described herein will affect the para-selectivity and alkylbenzene conversion. Such conditions include the temperature, pressure, space velocity, molar ratio of the reactants, and the hydrogen to hydrocarbon mole ratio ($H_2$/HC). For example, it has been observed that an increase in temperature can increase the activity of the modified catalyst. It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst.

A selectivated and steamed catalytic molecular sieve may be contacted with an alkylbenzene feedstock under conditions for effecting vapor-phase disproportionation. Conditions effective for accomplishing the high para-selectivity and acceptable alkylbenzene disproportionation conversion rates include a reactor inlet temperature of from about 200° C. to about 600° C., preferably from 350° C. to about 540° C.; a pressure of from about atmospheric to about 5000 psia (34.5 MPa), preferably from about 100 to about 1000 psia (0.69-6.89 MPa); a WHSV of from about 0.1 to about 20, preferably from about 2 to about 10; and a $H_2$/HC mole ratio of from about 0.05 to about 20, preferably from about 0.5 to about 6. This process may be conducted in either batch or fluid bed operation, with the attendant benefits of either operation readily obtainable. The effluent may be separated and distilled to remove the desired product, i.e., the para isomer, as well as other by-products. Alternatively, the appropriate fraction may be subjected to further separation, as in the case of xylenes, subjected to crystallization or the PAREX process to yield p-xylene.

The catalyst may be further modified in order to reduce the amount of undesirable by-products, such as, in the case of xylenes, ethylbenzene. The state of the art is such that the reactor effluent from standard toluene disproportionation typically contains from about 0.5% to about 2.5% ethylbenzene by-product. Upon distillation of the reaction products, the level of ethylbenzene in the C8s fraction often increases to between about 2% and 6%. This level of ethylbenzene is unacceptable for polymer grade p-xylene since ethylbenzene in the p-xylene, if not removed, degrades the quality of fibers ultimately produced from the p-xylene product. Consequently, ethylbenzene content of the p-xylene product must be kept low. The specification for the allowable amount of ethylbenzene in the p-xylene product has been determined by the industry to be less than 0.3%. Ethylbenzene can be substantially removed by crystallization, adsorptive separation, or by super fractionation processes.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the invention has been described above with reference to numerous embodiments and specific examples. Many variations will suggest themselves to those skilled in this art in light of the above detailed description. All such obvious variations are within the full intended scope of the appended claims.

What is claimed is:

1. A method for modifying a molecular sieve an intermediate pore-size molecular sieve comprising:
    treating a molecular sieve prepared by at least one ex situ silicon selectivation sequence to at least one in situ trim coke selectivation sequence to provide a modified silicon selectivated molecular sieve, wherein graphitic coke is adhered to said molecular sieve by said in situ trim coke selectivation sequence;
    wherein the method further comprises the step of hydrogen stripping the modified silicon selectivated molecular sieve; and
    wherein the in situ trim coke selectivation conditions comprise a reactor temperature of less than about 538° C., for about 0.1 hour to about 3 weeks, operating at a WHSV of about 0.1-20 hr$^{-1}$, and a hydrogen partial pressure of about 0.0689-2.07 Mpa-a, with a reactor pressure of about 1.72-2.41 Mpa-g.

2. The method of claim 1, wherein said molecular sieve is combined with a binder before any silicon selectivation sequence.

3. The method of claim 2, wherein said binder is at least one of $SiO_2$ and alumina.

4. The method of claim 1, wherein said ex situ silicon selectivation sequence comprises:
    contacting said molecular sieve with a silicon-containing selectivating agent comprising silicones or silicone polymers, to provide a silicon-treated molecular sieve;

calcining said silicon-treated molecular sieve to provide a calcined silicon selectivated molecular sieve;

optionally steam treating said calcined silicon selectivated molecular sieve.

5. The method of claim 1, wherein said molecular sieve has been modified by between two and six ex situ silicon selectivation sequences and including at least one steam-treating.

6. The method of claim 1, wherein said molecular sieve has been modified by two ex situ silicon selectivation sequences.

7. The method of claim 1, wherein said molecular sieve has been modified by three ex situ silicon selectivation sequences.

8. The method of claim 1, wherein the in situ trim coke selectivation conditions comprise a reactor temperature of about 454-510° C., operating at a WHSV of about 1-3 $hr^{-1}$ and a hydrogen partial pressure of about 0.276-0.827 Mpa-a.

9. The method of claim 1, wherein the silicon selectivation comprises the use of dimethylphenylmethyl polysiloxane.

10. The method of claim 1, wherein said molecular sieve comprises a zeolite having a Constraint Index from about 1 to about 12.

11. The method of claim 1, wherein said molecular sieve comprises ZSM-5.

12. The method of claim 11, wherein said molecular sieve comprises ZSM-5 having a crystal size larger than about 0.2 micron.

13. The method of claim 11, wherein said molecular sieve comprises ZSM-5 having a crystal size of about 0.2 micron or smaller.

14. The method of claim 1, wherein said molecular sieve contains no metals impregnated therein.

15. The method of claim 1, wherein said molecular sieve is incorporated with binder prior to in situ trim coke selectivation.

16. The method of claim 1, wherein said in situ trim coke selectivating step comprises contacting said molecular sieve with a thermally decomposable organic compound selected from linear paraffins, branched paraffins, cycloparaffins, linear olefins, branched olefins, cycloolefins, aromatics, alcohols, aldehydes, ethers, ketones, phenols, heterocyclics, and mixtures thereof, at a temperature in excess of the decomposition temperature of the thermally decomposable organic compound.

17. The method of claim 16, wherein said organic compound includes an alkyl-substituted benzene.

18. The method of claim 1, wherein said hydrogen stripping comprises contact of said modified silicon selectivated molecular sieve with hydrogen in the absence of hydrocarbon feed.

19. The method of claim 18, wherein said hydrogen stripping comprises contacting said modified silicon selectivated molecular sieve with hydrogen in the absence of hydrocarbon feed for about 12-48 hours, at a temperature range of 454-510° C. and a pressure of about 1.72-2.41 MPa-g.

* * * * *